United States Patent
Luo et al.

[11] Patent Number: 6,022,477
[45] Date of Patent: Feb. 8, 2000

[54] METHOD AND APPARATUS FOR ISOLATION PURIFICATION OF BIOMOLECULES

[75] Inventors: Robert G. Luo, Edison; Kamalesh K. Sirkar, Berkeley Heights, both of N.J.

[73] Assignee: New Jersey Institute of Technology, Newark, N.J.

[21] Appl. No.: 08/970,986

[22] Filed: Nov. 14, 1997

[51] Int. Cl.[7] .......................... B01D 11/00; B01D 15/08
[52] U.S. Cl. ............................. 210/645; 210/656
[58] Field of Search ............................ 210/656, 645, 210/198.2, 321.8, 321.89, 635

[56] References Cited

U.S. PATENT DOCUMENTS

| | | | |
|---|---|---|---|
| 4,206,050 | 6/1980 | Walch et al. | 210/646 |
| 4,960,692 | 10/1990 | Lentrichia et al. | |
| 5,124,041 | 6/1992 | Sheer et al. | |
| 5,139,668 | 8/1992 | Pan et al. | |
| 5,240,994 | 8/1993 | Brink et al. | |
| 5,505,841 | 4/1996 | Pirbazari et al. | |
| 5,567,615 | 10/1996 | Degen et al. | |
| 5,575,910 | 11/1996 | Karbachsch et al. | 210/321.75 |
| 5,618,418 | 4/1997 | Demmer et al. | |

FOREIGN PATENT DOCUMENTS

| | | |
|---|---|---|
| 1292952 | 12/1991 | Canada . |
| 0 249 932 A | 12/1987 | European Pat. Off. . |
| 542655 | 11/1992 | European Pat. Off. . |
| 2 510 412 A | 2/1983 | France . |
| 71-33290 | 5/1995 | Japan . |
| 1526183 | 9/1978 | United Kingdom . |
| 94 09889 | 11/1994 | WIPO . |

OTHER PUBLICATIONS

Aagesen et al., 1995, Gen. Eng. New, p–12, Apr. 1.
Agrawal et al., 1996,Biotech Bioengg., 52:539–48.
Belter et al., 1988, Bioseparations: Downstream Processing for Biotechnology, John Wiley & Sons, Inc.
Chang and Chase, 1996, Biotech. Bioengg., 49:204–16.
Darbre et al., Biochimica et Biophysica Acta, 1975, 393:201–4.
Dickerson, 1969, The Structure and Action of Proteins, 44, 52, Harper and Row Publisher.
Freeman et al., 1993, Bio/Technology, 11:1007–12.
Hirayama et al., 1990, Biochem. Biophys. Res. Com., 173:639–46.
Kaplan and Foster, 1971, Biochemistry, 10:630–6.
Lehninger, 1975, Biochemistry, 157, 162.
Longsworth et al., 1949, J. Phys. Colloid Chem., 53:126–35.
Molinari et al., 1990,Biotech. Bioengg., 36:572–80.
Nigam et al., 1988, Biotech. Prog., 4:166–72.
Radola, 1973, Biochimica et Biophysica Acta, 295:412–28.
Timasheff et al., 1960, J. Amer. Chem. Soc., 82:3157–61.
van Reis et al., 1991, Biotech. Bioengg., 38:413–22.
The Busy Researcher's Guide to Biomolecule Chromatography, 135, PerSeptive Biosystems, Inc., 1996.

*Primary Examiner*—W. L. Walker
*Assistant Examiner*—Richard W. Ward
*Attorney, Agent, or Firm*—Klauber & Jackson

[57] ABSTRACT

An apparatus and method for recovering bioproducts from a feed solution. In one embodiment, the apparatus includes a module housing, a membrane disposed in the housing for filtering the bioproducts from the feed solution, and an adsorbent bed disposed in the housing for retaining the bioproducts which permeate through the membrane, wherein the apparatus is adapted to allow fractionation and purification of the retained bioproducts from the bed by elution.

15 Claims, 6 Drawing Sheets

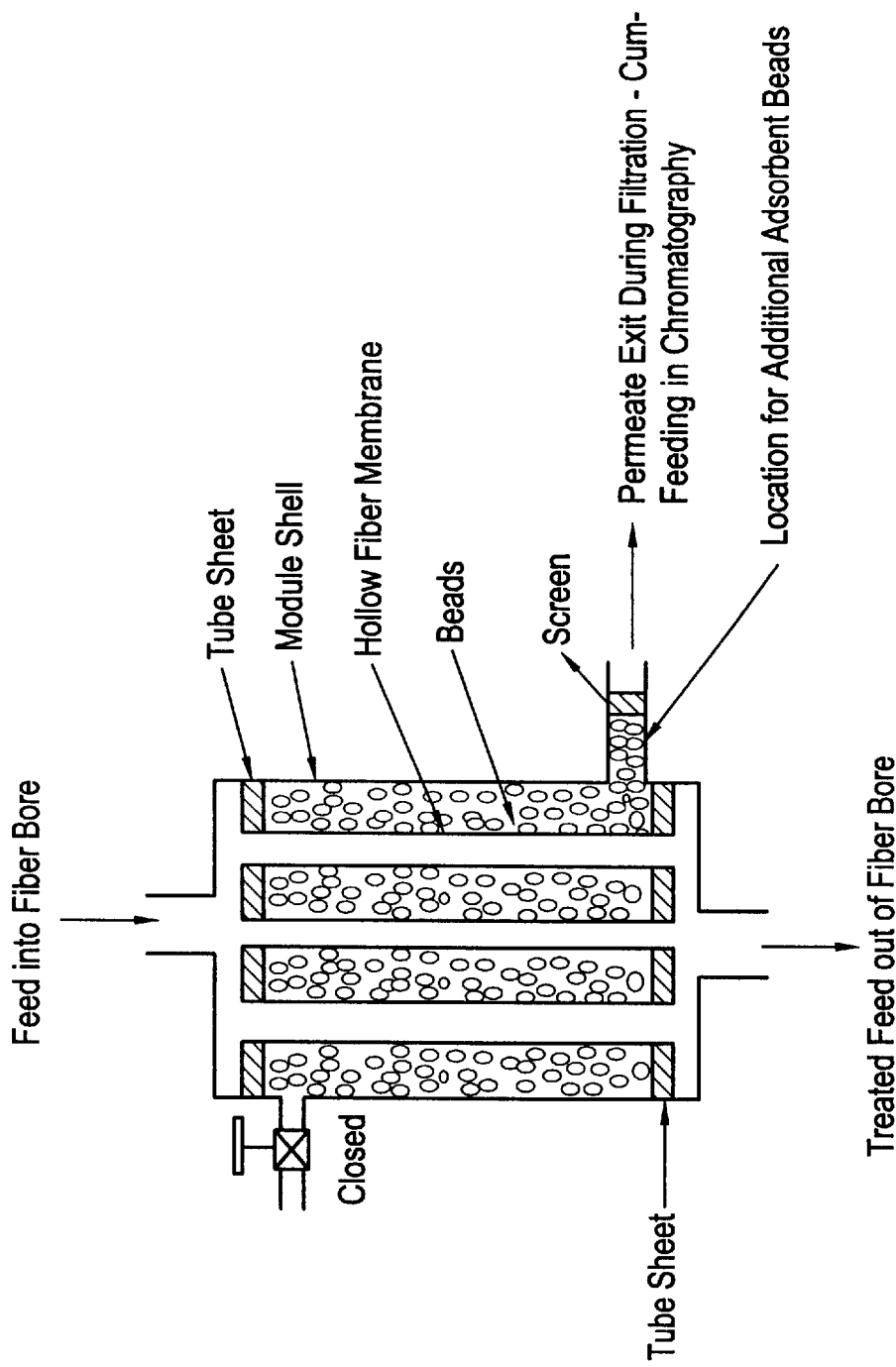

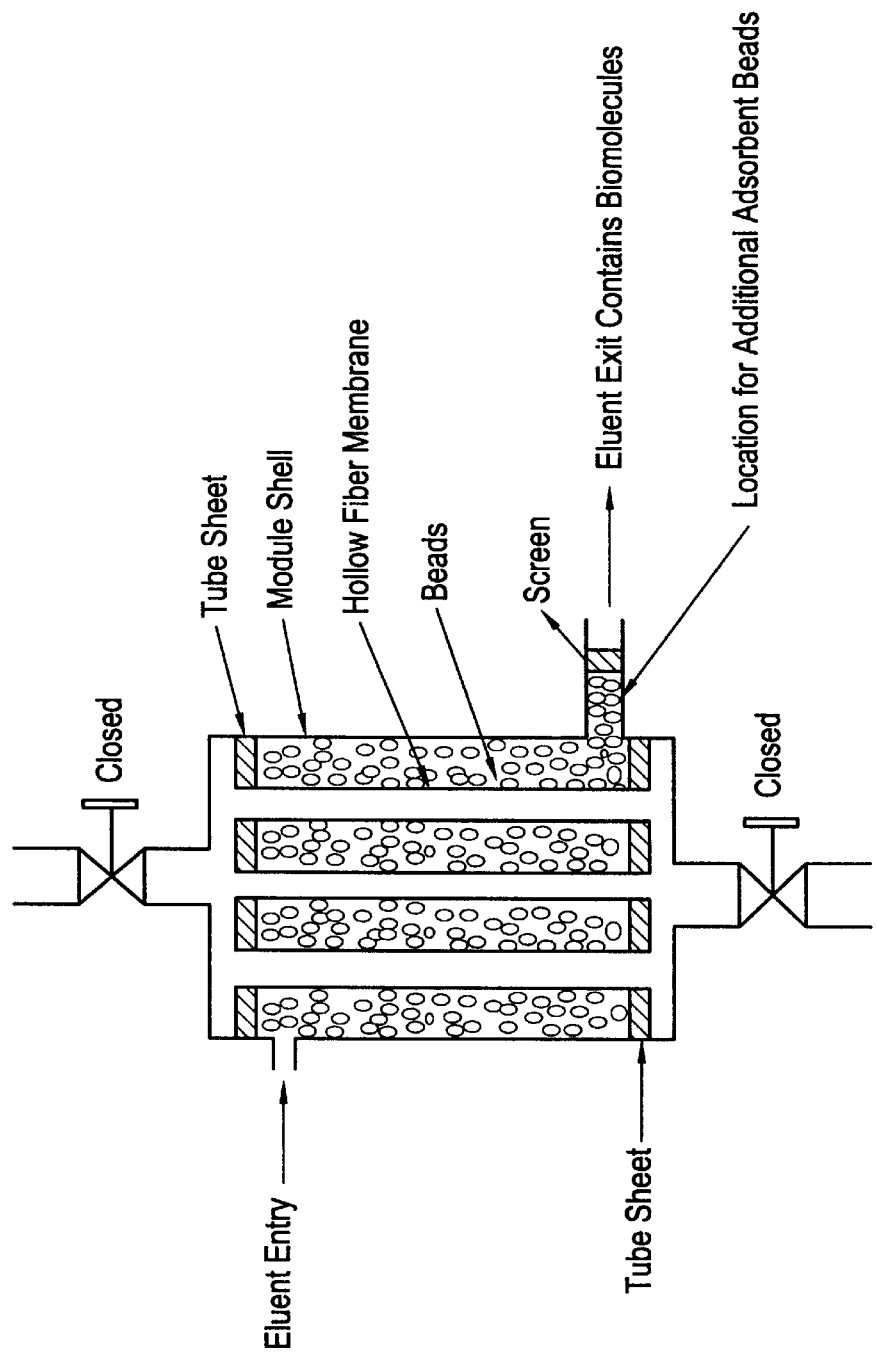

Alternative Configuration of the Device Containing Membrane and Adsorbent Beads during Elution Step in Chromatography

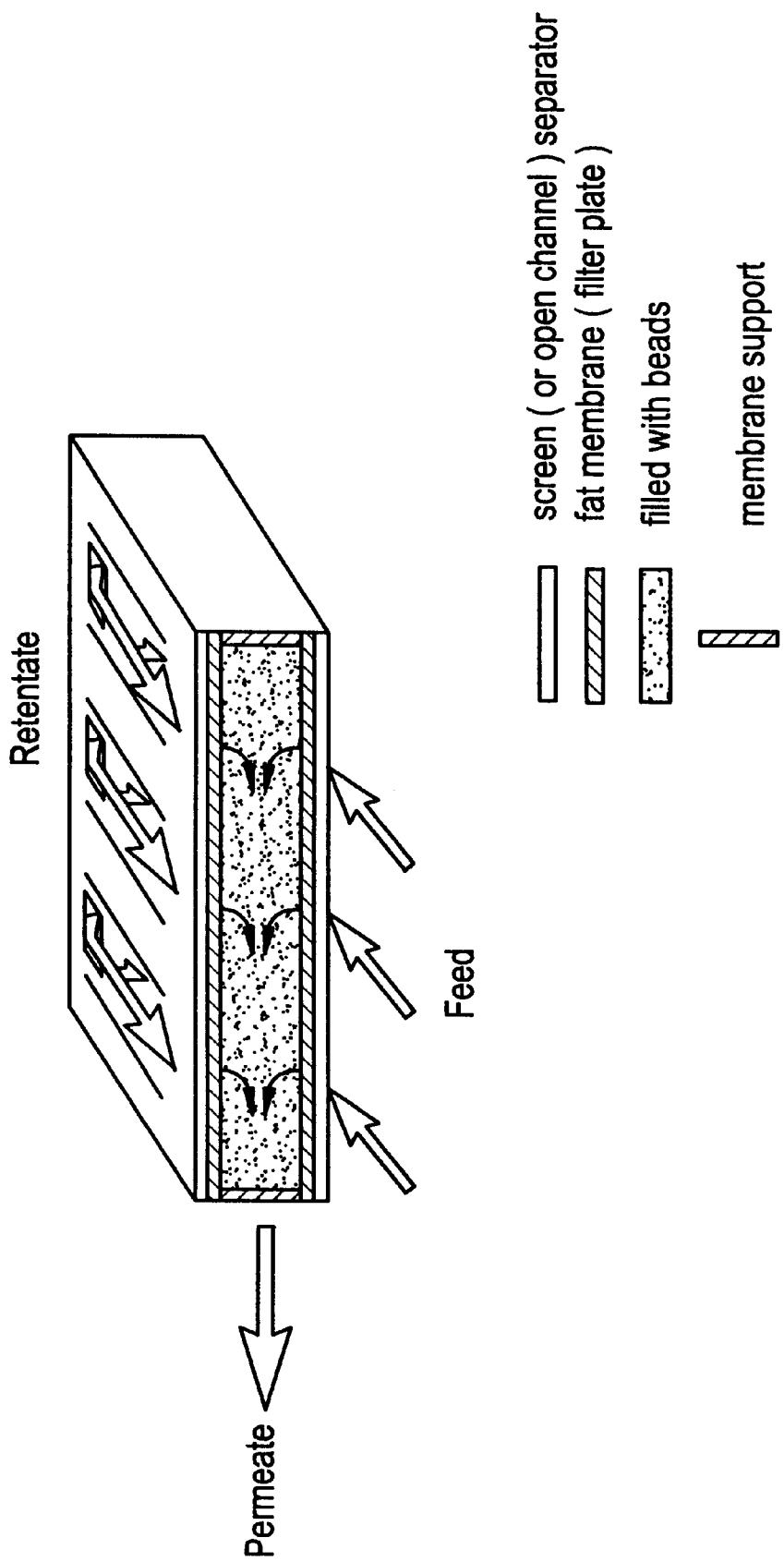

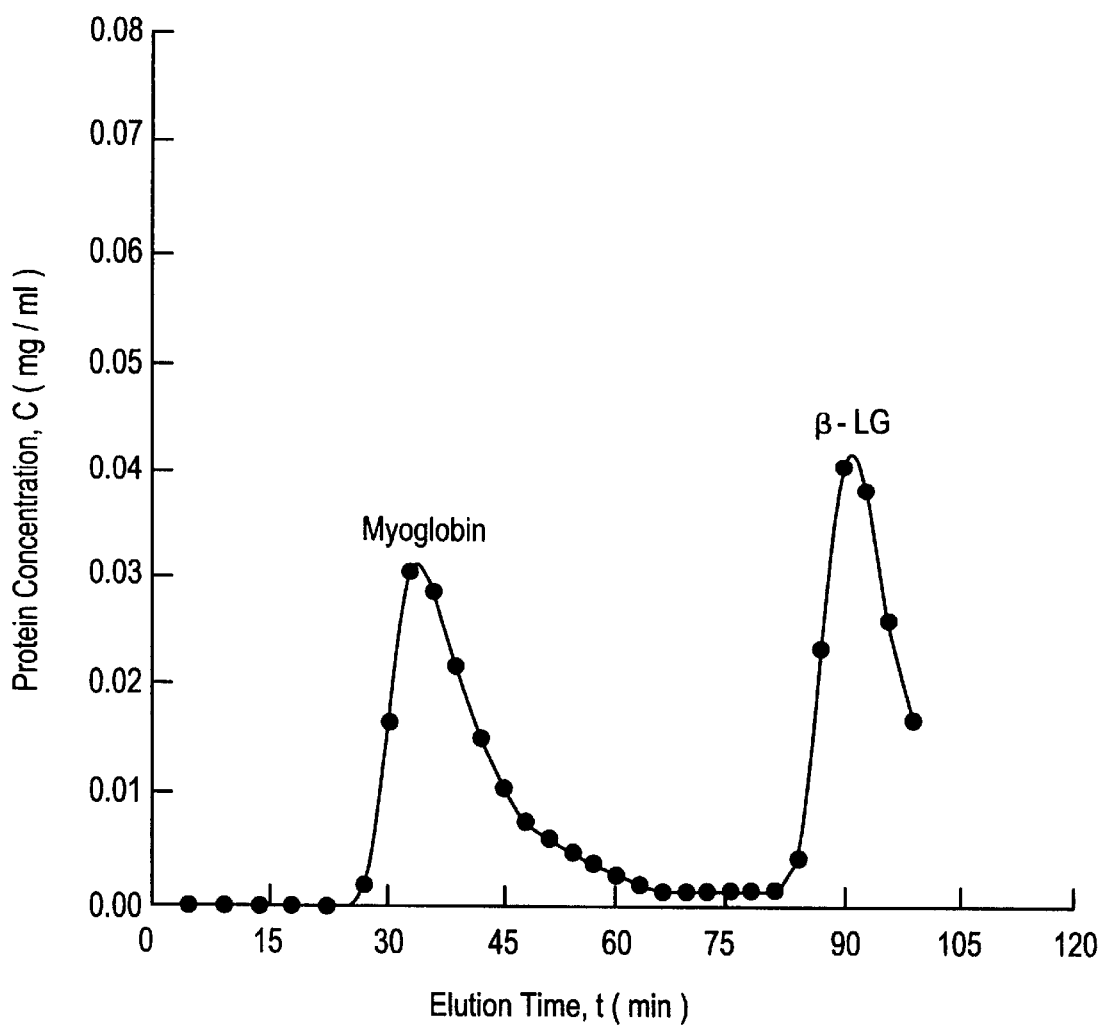

Separation of hemoglobin ( Hb ) and bovine serum albumin ( BSA )
Feed : 104.0 ml of a mixture of Hb ( 0.030 mg / ml ) and BSA ( 0.033 mg / ml ). Loading : through the tube side. Elution : 0 - 42 min, 0.05M NaCl in 20mM Tris - HCl ( pH8.0 ) ; 42 - 69 min, 0.1 M NaCl in Tris - HCl, 69 - 129 min, 0.2M NaCl in Tris - HCl. Flow rate : 1.845 ml / min.

METHOD AND APPARATUS FOR ISOLATION PURIFICATION OF BIOMOLECULES

FIELD OF THE INVENTION

The present invention relates to bioproduct or biomolecule separation generally and, more particularly, but not by way of limitation, to a novel method and apparatus for isolating and purifying biomolecules by membranes and adsorbents.

BACKGROUND OF THE INVENTION

Innovations in and improvement of bio-downstream processing, which is responsible for about 50–80% of recombinant proteins and other biomolecules, play a very important role in increasing the yield and reducing the cost of biopharmaceutical production. Biomolecule isolation and purification from a fermentation broth usually involve centrifugation, filtration, adsorption, and chromatography steps. Each step contributes to the product cost and product loss.

Bioproduct recovery from fermentation broths is complicated by the large number of dissolved substances and suspended particles present in the broth. Most bioseparation processes involve the following steps: removal of insolubles by either filtration or centrifugation, isolation of products using either adsorption or solvent extraction, purification (via chromatography and precipitation) and polishing via crystallization, or spray drying and lyophilization. For intracellular products, cell disruption is needed also to release the product before the removal of insolubles. See: Belter, P. A., Cussler, E. L. and Hu, W. *Bioseparations: Downstream Processing for Biotechnology*, John Wiley & Sons, Inc. (1988). Although the series of separation steps can usually accomplish the product recovery, reduction in the overall number of separation operations is desirable because of the low product yields associated with some steps. The development of techniques that reduce the overall number of steps are gaining popularity due to their reduced cost, increased yield and productivity along with the reduction in the complexity of the downstream processing flowsheets. See: Agrawal, A. and Burns, M. A., *Biotechnology and Bioengineering*, 52, 539 (1996); Chang, Y. K. and Chase, H. A., *Biotechnology and Bioengineering*, 49, 204 (1996); Freeman, A., Woodley, J. M. and Lilly, M. D., *Bio/Technology*, 11, 1007 (1993); and Molinari, R., Torres, J. L., Michaels, A. S., Kilpatrick, P. K. and Carbonell, R. G., *Biotechnology and Bioengineering*, 36, 572 (1990).

Biomolecules (e.g., interferons, hormones, immunoglobulins, growth factors, DNAs, etc.) obtained from large-scale fermentation and cell-culture processes may be present in low concentrations in a complex medium/broth containing various combinations of cells, cell fragments, lysed cells, colloidal materials, etc. For example, the medium may be a mixture of an aqueous solution and particles. By way of another example, the medium could be proteins dissolved in water. The nature of such heterogeneous aqueous solutions containing the biomolecules is influenced by the nature of the bioproduct, i.e., whether the product is extracellular or intracellular. In the case of intracellular products, cells are recovered from the broth; then cell lysis and homogenization are undertaken to produce a homogenate. The biomolecules are next separated from the cell debris by lysate clarification. In the case of extracellular products, the biomolecules are separated from the whole cells by clarification.

A number of different technologies or sequence of technologies can be employed to eliminate the cellular and colloidal material prior to bioproduct purification via adsorption/chromatography steps. These include centrifugation, flocculation, liquid-liquid extraction and various forms of microfiltration (dead-end, tangential flow and rotary). The devices involved in these processes are complex; there is significant loss of product at each step. See: van Reis, R., L. C. Leonard, C. C. Hsu and S. E. Builder, Industrial scale harvest of proteins from mammalian cell culture by tangential flow filtration, *Biotech. Bioengg.*, 38, 413 (1991). It would be of great use if a process and an apparatus were there to recover and purify the product biomolecule from the whole broth (for extracellular products) or a homogenate (for intracellular products) in one step.

Toward this one-step approach, three solutions have been suggested which employ specialized adsorbent beads/particles.

Nigam et al. (1988) have suggested using specially prepared immobilized adsorbents consisting of small, porous adsorbent particles entrapped within a reversible hydrogel matrix which excludes colloidal contaminants and suspended solids. See: Nigam, S. C., A. Sakoda and H. Y. Wang, Bioproduct recovery from unclarified broths and homogenates using immobilized adsorbents, *Biotech. Prog.*, 4(3), 166 (1988).

Chang and Chase (1996) have employed "streamline" adsorbents specially designed by Pharmacia Biotech (Uppsala, Sweden) for use in expanded bed adsorption of biomolecules from unclarified feedstocks. See the Chang, Y. K. and H. A. Chase, Ion exchange purification of G6PDH from unclarified yeast cell homogenates using expanded bed adsorption, *Biotech. Bioengg.*, 49, 402 (1996).

Aagesen et al. (1995) have designed beads incorporating dense inert particles so that they have a significantly higher density and can settle easily from an expanded fluidized bed after adsorbing the protein of interest from the solution; this technique has been identified as upfront chromatography (UFC) and the beads are identified as UpFront matrix. See: Aagesen, M., T. Wickborg and A. Lihme, Single-step initial protein purification with UpFront Chromatography, *Gen. Eng. News*, p-12, Apr. 1, 1995.

All of these aforementioned techniques require specially designed and costly adsorbents and/or unusual operational conditions in expanded/fluidized beds to accommodate the presence of an unclarified broth. More often than not, the specially designed bead may not have the required ion exchange or other ligands for the biomolecule separation from solution. On the other hand, microfiltration-based cell-protein separation or lysate clarification are being increasingly employed in small as well as large-scale harvesting of proteins and other biomolecules. Cf. van Reis et al. (1991), supra. Further, a wide variety of adsorbent beads or chromatographic matrix particles are commercially available and routinely used for biomolecule purification.

An object of the present invention is to efficiently integrate these functions into one device using commercially available and commonly utilized microfiltration membranes and adsorbent beads.

Various bioseparation-type devices have been proposed.

One type of device employs an adsorption bed with a hollow fiber housing, wherein a hollow fiber module was used as a housing for adsorbent beads, as described by Pan and McMinis in their U.S. Pat. No. 5,139,668 (1992), wherein adsorbent beads were "emplaced" on the tube side of the hollow fiber module, or, in another case, on the shell side of the module. The device was intended for gas or liquid separations and thus represented certain advantages over conventional packed bed elements or columns, including: the fluid pressure drop through the element is independent of the size of the particles because the fluid flow path through the fiber bore is separated from the particles in the case of particles on the shell side; very fine particles can, therefore, be used on the shell side; the microporous hollow fibers provide efficient and uniform contact between the adsorbent particles and the fluid mixture for a wide range of flow rates, etc. Thus, the hollow fiber modules provided a better housing for some adsorbent beads for certain applications as compared to the conventional packed bed adsorption columns. Notably, however, the hollow fibers were only used as the housing for adsorbent particles and the fibers themselves did not play any role in the separation. Further, no flow stream was ever taken out through the particle side.

Another approach to bioseparation involved the simultaneous ultrafiltration and affinity sorptive separation of proteins in a hollow fiber membrane module as reported by Molinari, R, J. L. Torres, A. S. Michaels, P. K. Kilpatrick and R. G. Carbonell, in "Simultaneous Ultrafiltration and Affinity Sorptive Separation of Proteins in a Hollow Fiber Membrane Module," *Biotechnol. Bioeng.*, 36, 572 (1990), wherein sorptive gel particles were loaded into the shell side of a hollow fiber membrane module, and the device was used in a process for simultaneous protein ultrafiltration and adsorption. In the process of Molinari et al., long binding times (seven hours in the example of horse serum cholinesterase, and five hours in the example of bovine liver carboxylesterase) were used to load proteins onto the adsorbent particles by recirculating the retentates, while the proteins were always present in the filtrates. At the end of the loading step, breakthrough occurred and the adsorbent bed was completely saturated by the protein. Furthermore, in the process of Molinari et al., the elution was conducted by permeating an eluent through the fiber lumen into the shell space. Since the bed was saturated by the feed protein, the desorption was similar to that in a conventional batch adsorption process. No chromatographic purification or fractionation took place.

However, in the present invention, as discussed herein, the mode of operation of the inventive device/process is appropriate for chromatographic fractionation of proteins through a bed of absorbents. Moreover, the chromatographic bed of the present invention is never saturated during the loading step.

Yet another type of device and process for bioseparation involves moving adsorbent particles through the lumen of membrane filters, wherein adsorbent particles binding the target compound are circulated through the lumen of a tubular microfiltration membrane or the lumen of a hollow fiber membrane module. The separation occurs when the compound bound to the particles is retained together with the particles and the compound not bound to the particles permeates through the membrane. This type of device and process were described in three patents by Byers et al., Canadian Patent 1,292,952 (1991), Degen et al., U.S. Pat. No. 5,567,615 (1996), and Pirbazari and Badriyha, U.S. Pat. No. 5,505,841 (1996) respectively. While the former two patents were aimed at biomolecule separations, the third was directed toward water decontamination. In Byers et al. (1991), for example, adsorbent beads were added to a mixture consisting of the target biomolecule and impurities, and the resulting solution was mixed to allow the adsorption of the target biomolecule onto the beads. The suspension was then circulated through the lumen of hollow fiber membranes. The target biomolecule was retained with the beads due to the large size of the beads. The impurities which were not bound to the beads permeated through the membrane to the shell space.

A principal object of the present invention is to provide a method and device for isolation and purification of biomolecules.

Another object of the present invention is to provide a method and apparatus which integrates clarification, concentration and separation of biomolecules into a single step or single device.

It is another object of the present invention to provide an apparatus and method which may be easily adopted for large scale processing.

Another object is to provide a hybrid bioseparation apparatus and process involving commercially available membranes and adsorbents.

A further object is to provide a bioseparation method and apparatus suitable for both extracellular and intracellular products.

Other objects of the present invention, as well as particular features, elements, and advantages thereof, will be elucidated in, or be apparent from, the following description and the accompanying drawing figures.

SUMMARY OF THE INVENTION

The present invention achieves the above objects, among others, by providing a novel method and apparatus for isolating and purifying biomolecules by membranes and adsorbents.

In one aspect, the present invention relates to a membrane module means for recovering bioproducts from a feed solution, the means including a module housing, membrane means disposed in the housing for filtering the bioproducts from the feed solution, and an adsorbent bed means disposed in the housing for retaining the bioproducts which permeate through the membrane means, wherein the membrane module means is adapted to allow fractionation and purification of the retained bioproducts from the bed by elution.

The present invention also contemplates a system comprising a plurality of such membrane module means. In one embodiment, for example, the system may include at least two of the modules are connected in parallel.

The present invention also relates to an apparatus for recovering bioproducts from a feed solution, wherein the apparatus comprises: a housing having a feed inlet means, a feed outlet means, and a permeate outlet means; at least one membrane means disposed within the housing and having a feed side and a permeate side; and a packed bed of adsorbent particles disposed within the housing in contact with the permeate side of the membrane. The feed inlet means allows the feed solution to pass into contact with the feed side of the membrane. The bioproducts are separated from the feed solution by permeation to the permeate side of the membrane means, and the permeated bioproducts contact the packed bed. The bioproducts are retained by the adsorbent particles. Thus, the bioproducts are isolated from the feed solution.

The apparatus may further include means to control the inlet flow of the feed solution. Thus, the introduction of feed solution into the feed inlet means may be terminated before the packed bed becomes saturated, or the introduction of feed solution into the feed inlet may be terminated before breakthrough of the bioproducts occurs at the permeate outlet means.

The bioproducts retained by the adsorbent particles are preferably capable of being eluted directly from the apparatus. Thus, in one embodiment, the housing is adapted to allow introduction of an elution solution, wherein the bioproducts are capable of being purified in situ by passing the elution solution over the adsorbent particles disposed in the membrane module. In another embodiment, the apparatus is adapted to allow an elution solution to pass through the membrane and into contact with the adsorbent particles in order to purify the retained bioproducts.

In one preferred embodiment, the membrane is a microfiltration membrane. In another preferred embodiment, the membrane is an ultrafiltration membrane.

In a preferred embodiment, the apparatus is a hollow fiber membrane module having at least one hollow fiber. Further preferably, a plurality of hollow fibers are provided in a module.

In the hollow fiber membrane module, the adsorbent particles are disposed on the shell-side of the hollow fiber, and the feed solution is passed through the tube-side of the hollow fiber.

The module is preferably provided with a permeate-side inlet means and a permeate-side outlet means.

In another preferred embodiment, the membrane module is a plate-and-frame membrane module.

In another aspect, the present invention relates to a method of recovering bioproducts from a feed solution, wherein the method comprises: providing a membrane module comprising a housing, at least one membrane disposed within the housing and having a feed side and a permeate side, and a packed bed of adsorbent particles disposed within the housing in contact with the permeate side of the membrane; passing the feed solution into the membrane module to contact the feed side of the membrane; and separating bioproducts from the feed solution by permeation through to the permeate side of the membrane and allowing the permeated bioproducts to contact the adsorbent particles, wherein the bioproducts are retained by the adsorbent particles, whereby the bioproducts are isolated from the feed solution.

In one preferred embodiment, the introduction of feed solution into the membrane module is terminated before the packed bed becomes saturated.

In another preferred embodiment, the introduction of feed solution into the membrane module is terminated before breakthrough of the bioproducts occurs at the permeate outlet of the membrane module.

The method further preferably includes eluting the bioproducts retained by the adsorbent particles disposed in the membrane module.

In a preferred embodiment, the method includes purifying the bioproducts by passing an elution solution over the adsorbent particles disposed in the membrane module.

In one embodiment, an elution solution may be passed through the membrane and into contact with the adsorbent particles in order to purify the retained bioproducts.

Preferably, the adsorbent particles reduce the differences in transmembrane pressure along the length of the feed solution flow path through the module.

In one preferred embodiment of the method, the membrane is a microfiltration membrane. In another preferred embodiment, the membrane is an ultrafiltration membrane.

In one preferred configuration, the membrane module is a hollow fiber membrane module having at least one hollow fiber. The adsorbent particles are preferably disposed on the shell-side of the hollow fiber, and the feed solution is passed through the tube-side of the hollow fiber. The hollow fiber preferably has an inner diameter in the range of 100 micrometer to 2000 micrometer.

In another preferred configuration, the membrane module is a plate-and-frame membrane module.

BRIEF DESCRIPTION OF THE DRAWINGS

Understanding of the present invention and the various aspects thereof will be facilitated by reference to the accompanying drawing figures, submitted for purposes of illustration only and not intended to limit the scope of the invention, in which:

FIG. 1a is a cross-sectional elevational illustrative view of a preferred embodiment during filtration-cum-feeding in chromatographic separation, in accordance with the present invention;

FIG. 1b is the preferred embodiment of FIG. 1a during shell-side elution in chromatography, in accordance with the present invention;

FIG. 1d is a perspective, partially cut-away view of an illustration of another preferred embodiment of the present invention in a flat membrane configuration;

FIG. 2 graphically illustrates experimental separation of myoglobin and β-Lactoglobulin via the present invention.

DETAILED DESCRIPTION OF THE PREFERRED EMBODIMENTS

Figure 1C:
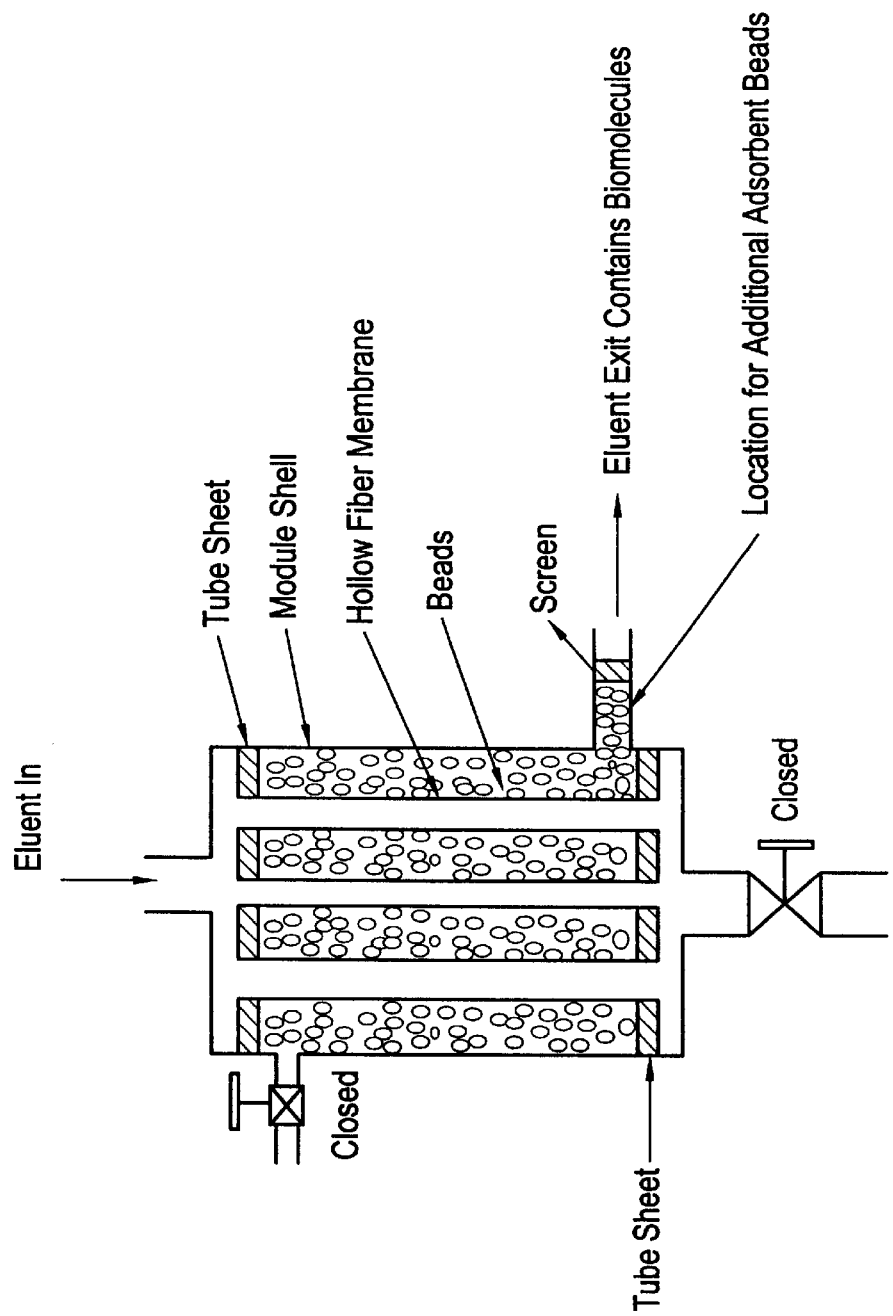
FIG. 1c is the preferred embodiment of FIG. 1a during tube-side elution in chromatography, in accordance with the present invention.

In one aspect, the present invention relates to a membrane module means for recovering bioproducts from a feed solution, the means including a module housing, membrane means disposed in the housing for filtering the bioproducts from the feed solution, and an adsorbent bed means disposed in the housing for retaining the bioproducts which permeate through the membrane means, wherein the membrane module means is adapted to allow fractionation and purification of the retained bioproducts from the bed by elution.

The present invention also contemplates a system comprising a plurality of such membrane module means. In one embodiment, for example, the system may include at least two of the modules which are connected in parallel.

The present invention also relates to an apparatus for recovering bioproducts from a feed solution, wherein the apparatus comprises: a housing having a feed inlet means, a feed outlet means, and a permeate outlet means; at least one membrane means disposed within the housing and having a feed side and a permeate side; and a packed bed of adsorbent particles disposed within the housing in contact with the permeate side of the membrane. The feed inlet means allows the feed solution to pass into contact with the feed side of the membrane. The bioproducts are separated from the feed solution by permeation to the permeate side of the membrane means, and the permeated bioproducts contact the packed bed. The bioproducts are retained by the adsorbent particles. Thus, the bioproducts are isolated from the feed solution.

The apparatus may further include means to control the inlet flow of the feed solution. Thus, the introduction of feed solution into the feed inlet means may be terminated before the packed bed becomes saturated, or the introduction of feed solution into the feed inlet may be terminated before breakthrough of the bioproducts occurs at the permeate outlet means.

The bioproducts retained by the adsorbent particles are preferably capable of being eluted directly from the apparatus. Thus, in one embodiment, the housing is adapted to allow introduction of an elution solution, wherein the bioproducts are capable of being purified in situ by passing the elution solution over the adsorbent particles disposed in the membrane module. In another embodiment, the apparatus is adapted to allow an elution solution to pass through the membrane and into contact with the adsorbent particles in order to purify the retained bioproducts.

In a preferred embodiment, the adsorbent particles are chromatographic matrix particles. The adsorbent particles may be adsorbent beads. In a particular embodiment, the adsorbent particles have an effective diameter of 5 micrometers or greater.

The adsorbent particles may also comprise affinity ligands attached thereto.

The adsorbent particles preferably reduce the differences in transmembrane pressure along the length of the feed solution flow path between the feed inlet means and the feed outlet means.

In one preferred embodiment, the membrane is a microfiltration membrane. In another preferred embodiment, the membrane is an ultrafiltration membrane.

In a preferred embodiment, the apparatus is a hollow fiber membrane module having at least one hollow fiber. Further preferably, a plurality of hollow fibers are provided in a module.

In the hollow fiber membrane module, the adsorbent particles are disposed on the shell-side of the hollow fiber, and the feed solution is passed through the tube-side of the hollow fiber.

The module is preferably provided with a permeate-side inlet means and a permeate-side outlet means.

The hollow fiber preferably has an inner diameter in the range of 100 micrometer to 2000 micrometer.

In another preferred embodiment, the membrane module is a plate-and-frame membrane module.

In another aspect, the present invention relates to a method of recovering bioproducts from a feed solution, wherein the method comprises: providing a membrane module comprising a housing, at least one membrane disposed within the housing and having a feed side and a permeate side, and a packed bed of adsorbent particles disposed within the housing in contact with the permeate side of the membrane; passing the feed solution into the membrane module to contact the feed side of the membrane; and separating bioproducts from the feed solution by permeation through to the permeate side of the membrane and allowing the permeated bioproducts to contact the adsorbent particles, wherein the bioproducts are retained by the adsorbent particles, whereby the bioproducts are isolated from the feed solution.

In one preferred embodiment, the introduction of feed solution into the membrane module is terminated before the packed bed becomes saturated.

In another preferred embodiment, the introduction of feed solution into the membrane module is terminated before breakthrough of the bioproducts occurs at the permeate outlet of the membrane module.

The method further preferably includes eluting the bioproducts retained by the adsorbent particles disposed in the membrane module.

In a preferred embodiment, the method includes purifying the bioproducts by passing an elution solution over the adsorbent particles disposed in the membrane module.

In one embodiment, an elution solution may be passed through the membrane and into contact with the adsorbent particles in order to purify the retained bioproducts.

The method may be practiced with adsorbent particles which are chromatographic matrix particles.

The method may be practiced with adsorbent particles which are adsorbent beads.

The adsorbent particles may have an effective diameter of 5 micrometers or greater.

The adsorbent particles may further include affinity ligands attached thereto.

Preferably, the adsorbent particles reduce the differences in transmembrane pressure along the length of the feed solution flow path through the module.

In one preferred embodiment of the method, the membrane is a microfiltration membrane. In another preferred embodiment, the membrane is an ultrafiltration membrane.

In one preferred configuration, the membrane module is a hollow fiber membrane module having at least one hollow fiber. The adsorbent particles are preferably disposed on the shell-side of the hollow fiber, and the feed solution is passed through the tube-side of the hollow fiber. The hollow fiber preferably has an inner diameter in the range of 100 micrometer to 2000 micrometer.

In another preferred configuration, the membrane module is a plate-and-frame membrane module.

Reference should now be made to the drawing figures, on which similar or identical elements are given consistent identifying numerals throughout the various figures thereof, and on which parenthetical references to figure numbers direct the reader to the view(s) on which the element(s) being described is (are) best seen, although the element(s) may also be seen on other views.

FIGS. 1a–1c illustrate one preferred embodiment of the present invention. It should be noted, however, that the present invention may be manifested in a variety of embodiments, and the examples described herein are merely illustrative and are not intended to be limiting. For example, virtually any microfiltration (MF) or ultrafiltration (UF) device, such as may be in the hollow fiber form, or in a plate-and-frame, or spiral-wound, or other configuration.

Referring again to FIGS. 1a–1c, the shell-side of a hollow fiber device may be packed with adsorbent beads commonly used in biomolecule adsorption or chromatography in order to recover and fractionate any mixture of biomolecules/proteins from a lysate or a whole cell broth in one device. The cell lysate or broth or whole cell suspension can be passed through the tube-side of the device as in tangential flow filtration. The solution permeating through the membrane pores and appearing on the shell side of the membrane device at every location will contact the adsorbent beads. The protein or the biomolecule of interest will be adsorbed on the surfaces and pores of the beads from the permeated solution as it flows through the packed shell side and leaves through the shell-side exit. Typically, two shell-side exit ports are provided in a hollow fiber-based shell-and-tube device. In the embodiment of the present invention shown in FIG. 1a, the shell-side exit on the furthest side from the tube-side inlet can be used for permeate exit. The other exit outlet should, preferably, remain closed during this operation.

This mode of operation of microfiltration-cum-chromatographic adsorption may be preferably carried out for a period long enough to substantially utilize the packed adsorbent bed capacity without achieving a breakthrough of the biomolecule through the permeate exit. In order to prevent breakthrough, the concentration of biomolecule at the permeate exit can be, for example, monitored by an on-line detector (e.g. a UV detector) or predicted by a mathematical model. Then the operation of membrane microfiltration is to be stopped. The elution of the adsorbed biomolecule may be initiated next by opening the permeate side exit port which is kept closed during the microfiltration-cum-adsorption process. As illustrated in FIG. 1b, an eluent may then be passed through the shell-side of the packed bed, and the eluent containing the desorbed biomolecule can exit by the shell-side exit port used in the adsorption part of the cycle for permeate exit.

As shown in FIG. 1b, during this operation of elution of the adsorbed biomolecule from the adsorbent beads packed on the shell-side of the hollow fiber device, the two tube-side outlets, i.e., the inlet and the exit of the hollow fibers, should preferably remain closed.

FIG. 1c illustrates an alternate operational mode for elution which involves introducing the eluent through the hollow fiber inlet employed for broth introduction as seen in FIG. 1a and taking the eluent out through the permeate outlet employed during microfiltration-cum-chromatographic adsorption. However, the broth outlet end of the hollow fiber used during microfiltration-cum-adsorption will remain closed.

The unusual combination of microfiltration-cum-chromatographic adsorption in one hollow fiber device provided by the present invention yields some unexpected advantages.

First, if the feed contains three or more types of biomolecules, which can be separated by a UF membrane, the device/process of the present invention will allow individual recovery/purification of such biomolecules permeating through the membrane by employing the present invention.

Second, the membrane units employed for MF/UF are modular; hence, the adsorbent bed can be modular, thereby eliminating the problem of scaleup. For example, more than one packed hollow fiber module (HFM) may be used in parallel operation.

Third, unless the permeate side pressure drops for a certain condition are excessive, most commercially available beads can be used in such a device/process.

Fourth, due to the presence of the packings on the shell side, the permeate which enters close to the tube-side feed inlet undergoes much more pressure drop than the permeate which enters the shell side near the tube-side feed outlet. As a result, the transmembrane pressure difference along the membrane length is much more uniform than otherwise. Further, the possibility of reverse filtrate flow at the feed outlet region can be eliminated.

Fifth, any biomolecule that has been adsorbed on the membrane surface/pores may be recovered by carrying out elution through the tube-side inlet, as shown in FIG. 1c.

In conventional hollow fiber modules, there is often bypassing and channeling of the liquid on the shell-side. Such bypassing is eliminated here with the present invention since the void volumes are filled with adsorbent beads. Thus, adsorption of permeated protein from the permeate should be quite efficient. Similarly, the fibers can facilitate more uniform packing of the beads on the shell side than that in conventional chromatographic devices. Similarly, the elution process is less likely to suffer from bypassing or channeling. However, there may be a possibility in particular situations where the adsorption of the biomolecule in the permeate produced near the feed outlet may not be sufficient since at this location the permeate is essentially flowing radially outward. Under such conditions, it may be desirable to add an optional small packed section to the shell-side permeate outlet connection, as seen in FIGS. 1a, 1b and 1c.

As illustrated in FIG. 1d, the present invention can also be easily manifested in a flat membrane geometry. In FIG. 1d, the permeate exit on the right hand side is blocked in order to carry out the elution chromatographic process. In addition, screened and open channel separators can be placed in the bead area to provide additional support to the membranes. The permeate channels may be conveniently filled with adsorbent beads.

Thus, in a hollow fiber device, the shell side may be packed with beads by a simple filtration process. The tube-side inlet and outlet are to be closed. Then a slurry of the beads is to be pumped into the shell side from one of the shell-side outlets; the other shell-side outlet should have a screen to hold the beads in place as water goes out through the screen. A similar procedure may be followed for flat membrane devices. Such procedures may be implemented in a laboratory scale or production scale without great difficulty.

Hollow fiber or flat membrane modules can be cleaned-in-place (CIP) or sanitized by an appropriate sequence of cleaning solutions (see, for example, van Reis et al. (1991)). The adsorbent particles may be similarly subjected to a CIP procedure (see, for example, Chang and Chase (1996)). One has to ensure that these two procedures are reasonably compatible. To avoid unwarranted introduction of a cleaning solution from one side (e.g., tube side) to the other side (e.g., shell side) in case of some incompatibility, the inlet as well as the exit on the other side should be kept closed, if needed.

The vast majority of conventional hollow fiber membrane-based ultrafiltration and microfiltration devices could be utilized in the present invention. Associated fiber dimensions may vary from 100 $\mu$m I.D. upwards to 2000 $\mu$m I.D. or even higher. The adsorbent beads that are usable with this invention may be 5 $\mu$m and upwards. The adsorbent beads can have any functionality and can have any structure as long as they can stand the small pressure drop (2–5 psi) on the shell side.

Thus, the present invention can achieve protein/biomolecule recovery from a broth through a microfiltration membrane and its subsequent separation/purification by adsorption on beads on the permeate side of the microfiltration membrane. Furthermore, a mixture of two or three proteins or other biomolecules in a feed can be fractionated by employing an ultrafiltration membrane in the configuration of FIGS. 1a–1c. The UF membrane will hold larger biomolecules back and allow smaller biomolecules to go through. These permeated biomolecules may then be adsorbed and separated by chromatographic process by the adsorbents on the permeate side of the device. The present invention may also be used with a cellular broth.

FIG. 1a illustrates the process of loading of the feed solution on the adsorbent bed of the present invention. This loading process differs from loading in both axial flow (conventional) chromatography/adsorption columns and radial flow chromatography columns.

In an axial flow column, the feed is directly loaded on the top part of the adsorbent bed. In a radial flow column, the feed is loaded on the side part of the adsorbent bed via a flow perpendicular to the length of the porous support of the adsorbent bed. In the present invention, the feed is also loaded on the side part of the absorbent bed, but via a tangential flow at the tube side of the hollow fibers as well as by axial flow on the permeate side. Thus, biomolecules permeate through the membrane due to transmembrane pressure and diffusion, and the permeated stream appears radially into the packed bed but immediately flows down the column. It should be noted that the present invention can be operated (including loading, filtration and elution) in different positions such as vertical, horizontal or at some angle, although the vertical orientation is the preferred operating position.

As illustrated in FIGS. 1b and 1c, the elution of biomolecules adsorbed in the adsorbent bed can be carried out through either the shell side or the tube side of the hollow fiber module, respectively. The elution through the shell side is similar to that in axial flow column. In the case of elution through the tube side, the eluent flows in the radial direction first, then the eluent flow takes place in the axial direction.

Experimental Results

To demonstrate the utility of the invented process concept and apparatus, experiments were carried out in a hollow fiber membrane module (HFM) to separate the component proteins from binary protein mixtures. The preferred embodiment of the present invention combined the processes of filtration and chromatography into one device or into one hybrid process. A commercially available polysulfone hollow fiber ultrafiltration cartridge was selected based on its molecular weight cut off (MWCO) and the pore size compared with the size of the targeted products to be separated from the broth. Appropriate adsorbent beads were carefully packed in the shell side of the hollow fiber cartridge. The feed solution flowed through the fiber lumina. Particles or compounds in the broth and/or the protein mixtures in solution larger than the membrane pores were rejected and concentrated during filtration, while the smaller components went through the pores under appropriate transmembrane pressure and were then partitioned onto the adsorbent under proper conditions. Washing and elution was then conducted thereafter in particular ways to fractionate the biomolecules from the shell side.

In addition to combining several downstream steps such as clarification, concentration and purification into one device, the filtration-chromatography process and device of the present invention was found to have the following unique characteristics: 1) due to the presence of the beads on the shell side, the transmembrane pressure difference along the membrane length is much more uniform, and the possibility of reverse filtration flow at the feed outlet region may be significantly reduced; 2) the loading of feed solution on the adsorbent bed is different from that in either axial flow (conventional) chromatography/adsorption column or radial flow chromatography column, wherein the bed need not be saturated, and the loading via permeate can be carried out for a brief period only as in a chromatographic process; and 3) the elution can be carried out on the shell side under a pseudo-chromatographic mode for biomolecule fractionation and purification. The elution can also be carried out through the tube-side inlet so that the biomolecules adsorbed on the membrane surface/pores may be recovered, as illustrated in FIG. 1b.

Ion exchange chromatography was used to demonstrate this technique because it is widely used in the separation proteins; the relatively mild binding and elution conditions allow high protein recovery with intact biological activity. It plays a critical role in the purification of many proteins, antibodies, nucleic acids, and to a lesser extent peptides. See *The Busy Researcher's Guide to Biomolecule Chromatography*, 135, PerSeptive Biosystems, Inc. (1996). Hemoglobin (Hb, MW 64677 and bovine serum albumin (BSA, MW 66430 as well as myoglobin (MG, MW 17566 and β-lactoglobulin (β-LG, MW 35500) were selected for model protein mixtures due to their differences in pI values. See: Dickerson, R. E., *The Structure and Action of Proteins*, 52, Harper and Row Publisher (1969); Hirayama, K., Akashi, S., Furuya, M. and Fukuhara, K., *Biochemical and Biophysical Research Communications*, 173, 639 (1990); *Biochemica et Biophysica Acta*, 393, 201 (1975); and Townend, R., Weinberger, L. and Timasheff, S. N., *J. Amer. Chem. Soc.*, 82, 3157 (1960). The pI values for Hb, BSA, MG and β-LG are respectively 6.8, 4.7, 7.3 and 5.3. See: Lehniger, A. L., *Biochemistry*, 162 (1975); Longsworth, L. G. and Jacobsen, C. F., *J. Phys. Colloid Chem.*, 53, 126 (1949); Radola, B. J., *Biochemica et Biophysica Acta*, 295, 412 (1973); and Kaplan, L. J. and Foster, J. F., *Biochemistry*, 10, 630 (1971).

A hollow fiber membrane system QuixStand™ System was purchased from A/G Technology (Needham, Mass.). The hollow fiber cartridge is made of an ultrafiltration membrane having a 100,000 nominal molecular weight cut-off (NMWCO). DEAE-Sepharose Fast Flow beads were purchased from Pharmacia Biotech (Piscataway, N.J.). It has an average particle size of 90 μm. Model proteins, hemoglobin (Hb), β-lactoglobulin (β-LG), myoglobin and bovine serum albumin (BSA) were also purchased from Sigma.

The hollow fiber membrane cartridge (UFP-100-E-1A, MWCO 100,000; A/G Technology Corp., Needham, Mass.) was 36.2 cm long with 1.9 cm O.D. and 1.524 cm I.D., and contained 50 polysulfone fibers (25.4 cm long, 1.6 mm O.D. and 1.0 mm I.D.).

All other chemicals and materials were obtained commercially and were of the highest available quality. The starting buffer was 20 mM Tris-HCl, pH 8.0. All protein solutions were prepared using the starting buffer. Elution buffers were prepared by adding different amounts of NaCl into the starting buffer.

The spectrophotometer used to measure protein concentration was U-2000 equipped with a cell path length 10 mm (Hitachi, Danbury, Conn.) and quartz cuvets (S-10) (Sigma). The pumps used in filtration, washing, elution, regeneration and cleaning steps were Masterflex Model 7518-60 and 7518-10 (Cole Parmer, Chicago, Ill.).

The ethanol solution from the bottle containing the beads was decanted. The beads were equilibrated with the starting buffer. The membrane cartridge was cleaned and soaked with the starting buffer before packing. The dilute bead solution was pumped from the shell-side inlet; the shell-side outlet was blocked by a filter to hold the beads and let the buffer pass through. This packing was continued until the shell side was full of beads. The beads were equilibrated with the starting buffer if necessary. The resulting device is represented by FIG. 1a. To check if the adsorbent bed was properly packed, 1–3 ml of a protein mixture (MG and β-LG) were loaded onto the bed from the shell-side inlet in initial experiments. The bed was washed with starting buffer first. The elution was then conducted with a stepwise change of NaCl concentration (0.05 M to 0.5 M) in the starting buffer. Fractions were collected every 3 minutes and assayed for the protein concentrations.

For the filtration-cum-chromatography experiments of interest, 100–200 ml protein mixture solution was directly loaded from the tube-side inlet. The permeate and the retentate could be recycled if necessary, as understood, for example, from FIG. 1a. Elution was carried out from the shell side with two stepwise changes of NaCl concentration (0.05 M to 0.1 M, then 0.1 M to 0.2 M) in the starting buffer. Fractions were collected every 3 minutes and assayed for the protein concentrations. After each experiment, the bed was regenerated with 1.0 M NaCl in starting buffer (flow rate, 3–4 ml/min). The whole cartridge was cleaned with 0.5 M NaOH at 45–55° C.) and then the column was equilibrated with the starting buffer before storage at 4° C.

The concentrations of Hb, BSA, MG and β-LG were determined by measuring the absorbance at 430 nm and 280 nm. Concentrations of Hb and MG were directly measured from their standard curves at 430 nm; the concentrations of BSA and β-LG were obtained by their own absorbance at 280 nm which could be obtained by subtraction of the corresponding 280 nm absorbance of Hb and MG (calculated from their concentrations with standard curves at 280 nm) from the mixture absorbance at 280 nm.

Initial experiments utilized shell-side feed. A 1.0 ml mixture of MG (0.7 mg/ml) and β-LG (0.7 mg/ml) was loaded directly onto the shell-side bed followed by stepwise elution with 0.05 M NaCl in 20 mM Tris-HCl (pH 8.0) for the first 60 minutes, and with 0.5 M NaCl for the following 40 minutes. The elution flow rate was 1.65 mil/min. The beads were positively charged. Both proteins were negatively charged at pH 8.0.

FIG. 2 shows the separation of myoglobin and β-LG via shell-side loading. In this case, the feed was a mixture of myoglobin and β-LG in Tris-HCl buffer (pH 8.0). To check if the adsorbent bed was properly packed, the protein mixture was loaded directly on the bed in the shell side. Stepwise elution was used with a step change of NaCl concentration. A good separation was obtained as shown in the elution profile of FIG. 2. The first peak is of MG due to the weak interaction between the beads and MG. The second peak is of β-LG; the interaction between the beads and this protein was stronger. The resolution achieved was about 2.28. The good separation indicated that the packed beads in the shell side were working well as an anion exchanger.

Figure 3:
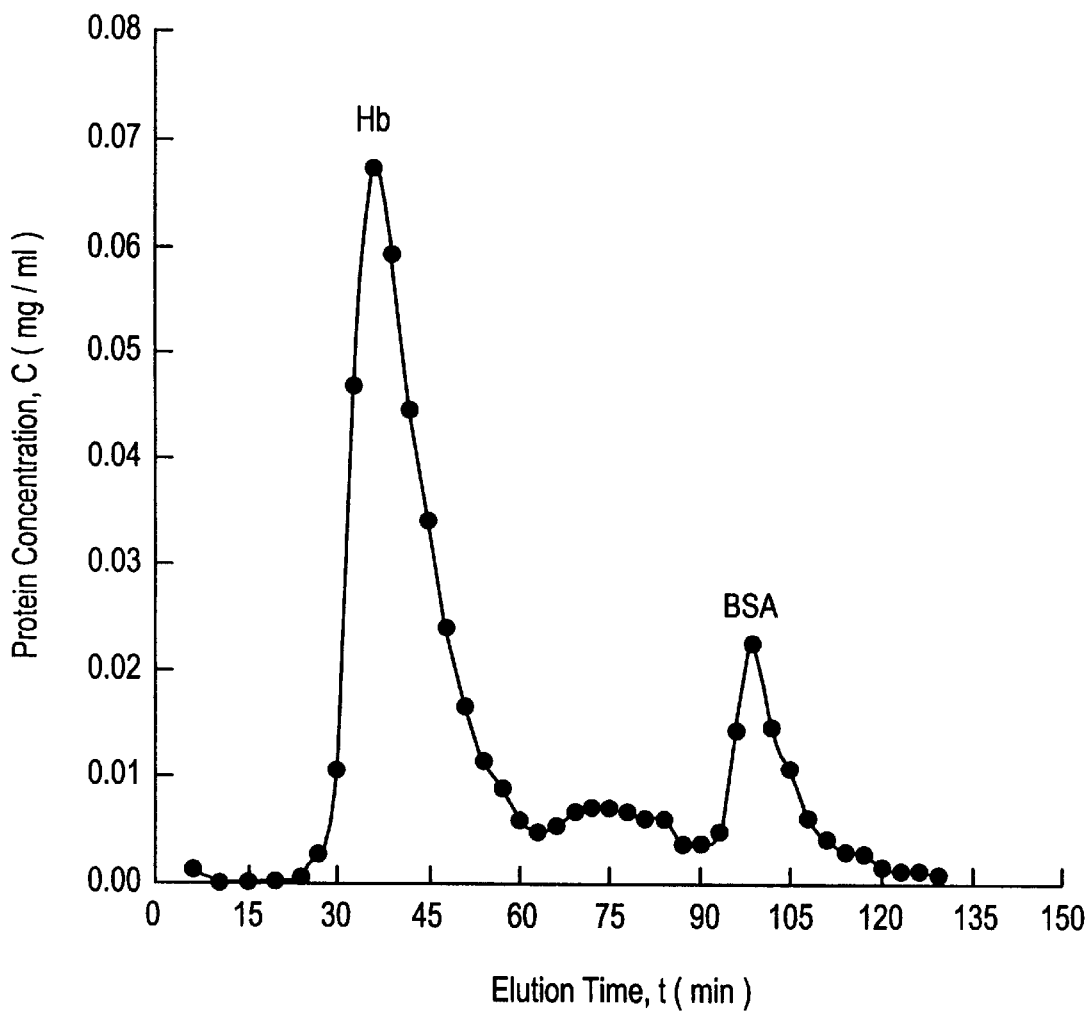
FIG. 3 graphically illustrates experimental separation of hemoglobin and bovine serum albumin via the present invention.

Filtration-cum-chromatography experiment was conducted next. FIG. 3 shows the separation of hemoglobin (Hb) and BSA. The feed mixture of Hb and BSA was loaded through the tube side, which is the normal loading procedure in the illustrated embodiment of the present invention. An aqueous solution of 0.030 mg/ml Hb and 0.033 mg/ml BSA in the starting buffer was pumped through the hollow fiber bores. The tube-side pressure was higher than that of shell side to maintain a certain transmembrane pressure. Full recycle was performed to return both permeate and retentate to the reservoir. Filtration-cum-feeding was run for 12 minutes at a permeate flow rate of 9.1 ml/min–13.6 ml/min, as illustrated in FIG. 1a. Since the molecular weights of Hb and BSA were smaller than the MWCO of the membrane, both Hb and BSA could partially pass through the pores of the membrane under the transmembrane pressure. The protein mixture was then fractionated by an elution run with two stepwise changes of NaCl concentration in the starting buffer. The elution was carried out in the shell side, as shown in FIG. 1b. The results in FIG. 3 show that the instant process and apparatus work quite well for the protein separation. A stepwise elution method was carried out: first (1) with 0.05 M NaCl (20 mM Tris-HCl, pH 8.0, 42 min), then (2) with 0.1 M NaCl (20 mM Tris-HCl, pH 8.0, 27 min), followed by elution (3) with 0.2 M NaCl (20 mM Tris, pH 8.0, 60 min) at a flow rate of 1.845 ml/min.

The experimental results suggest that: 1) it is possible to separate mixtures of proteins efficiently using an integrated filtration-cum-adsorption-cum-chromatography membrane system in one device; 2) it should be easy to scale up the process by providing a number of modules in parallel; and 3) other manifestations and geometrical configurations according to the present invention could be designed easily and used for biomolecule separation. The present invention can be easily applied to the direct separation of proteins from a cellular broth.

Thus, a hollow fiber ultrafiltration cartridge was successfully packed on the shell side with DEAE Sepharose Fast Flow anion exchange beads for separation of biomolecules via an integrated filtration-cum-chromatography process, and mixtures of MG and β-LG were efficiently separated in the shell-side bed which acted as an ion exchange chromatographic column. Mixture of Hb and BSA were separated through the integrated filtration-cum-chromatography process of the present invention.

The present invention may also be used with, for example, a feed solution of two or three proteins in an unclarified broth or a homogenate flowing through the tube side would be straightforward.

The present invention could also comprise hollow fibers or flat membranes having functional groups attached to the pore surfaces; in such a case, the pore surfaces could provide additional adsorption capacity or selectivity beyond that available in the bed of adsorbents incorporated in the permeate side of the ultrafiltration/microfiltration module.

Furthermore, the present invention is also applicable to centrifugally driven ultrafiltration/microfiltration processes. By way of example, the present invention can be used to isolate, recover and partially purify proteins and other factors from the milk of transgenic animals; in particular, ultrafiltration membranes would be employed in such applications.

Additionally, pores in microfiltration membranes may have grafted affinity ligands, e.g., protein A to adsorb appropriate proteins/antibodies from the permeate flowing through the pores.

Thus, the present invention provides an improved process and device over known devices.

For example, in contrast to Pan and McMinis, supra, the hollow fibers in the present invention are used not only as a housing for the beads, but also as a micro-/ultra-filtration device; both aspects are important in the instant invention. Further, the present invention provides a stream flowing out from the particle side of the housing.

In contrast to Molinari, supra, the loading via permeate is carried out for the present invention for a brief period only as in a chromatographic process. For example, the loading of the feed only took about 10 minutes in the separation of hemoglobin and bovine serum albumin. Protein is absent in the permeate during the loading step. Further, no breakthrough is allowed to occur and the adsorbent bed is never saturated. In addition, the concentration profile of the biomolecule on the adsorbent bed could be quite unique. Furthermore, the elution can be carried out not only through the tube-side inlet (i.e., through the fiber lumen into the shell space) in one case, but also through the shell-side inlet in another case. This shell-side elution can be conducted under a pseudo-chromatographic mode and can be used for biomolecule purification as well as fractionation.

In addition to the differences above, an unexpected advantage with regard to the transmembrane pressure difference in the present invention involved the pressure drop across the absorbent bed on the shell side of the hollow fiber module, i.e. the transmembrane pressure difference along the membrane length was much more uniform. As a result, membrane fouling can be significantly reduced and the flow rate of the feed liquid entering the bed along its length is quite uniform, leading to a more uniform loading of the beads.

Mathematical modeling was also used to describe the pressure profiles on both the tube side and the shell side, and the model solutions showed that the uniformity of the transmembrane pressure along the membrane length is better achieved with the beads than without the beads on the shell side. Further, the possibility of reverse filtration flow at the feed outlet region may be eliminated.

In contrast to the present invention, the type of device described by Byers et al., supra, involves the following: (1) the adsorbent particles move through the lumen of the membrane fibers during the process, as opposed to the adsorbent particles of the present invention being packed in the shell space of the membrane fibers; (2) the adsorption of the target compound onto the adsorbent particles takes place in a container before the filtration, as opposed to the present invention wherein adsorption of the target biomolecule onto the adsorbent particle takes place on the shell side of the hollow fiber module after the micro-/ultra-filtration process has occurred; and (3) a particular type of adsorption process is utilized, namely a moving bed adsorption process, versus the chromatographic process based on elution chromatographic technique of the present invention.

References cited herein are hereby incorporated by reference in their entirety.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

What is claimed is:

1. A method of recovering bioproducts from a feed solution, the method comprising:

providing a membrane module comprising a housing, at least one hollow fiber membrane disposed within the housing and having a feed side and a permeate side, a permeate outlet which extends outside of said housing, and a continuous packed bed of adsorbent particles in contact with the permeate side of said membrane, said particles being disposed within the housing and extending outside of said housing into said permeate outlet;

passing the feed solution into the membrane module to contact the feed side of the membrane;

separating bioproducts from the feed solution by permeation through to the permeate side of the membrane and allowing the permeated bioproducts to contact the adsorbent particles, wherein the bioproducts are retained by the adsorbent particles, whereby the bioproducts are isolated from the feed solution; and fractionating and purifying the retained bioproducts from the bed by chromatographic elution.

2. The method according to claim 1 wherein the membrane module is a hollow fiber membrane module having at least one hollow fiber.

3. The method according to claim 2 wherein the adsorbent particles are disposed on the shell-side of the hollow fiber, and wherein the feed solution is passed through the tube-side of the hollow fiber.

4. The method according to claim 2 wherein the hollow fiber has an inner diameter in the range of 100 micrometer to 2000 micrometer.

5. The method according to claim 1 further comprising terminating the introduction of feed solution into the membrane module before the packed bed becomes saturated.

6. The method according to claim 1 further comprising terminating the introduction of feed solution into the membrane module before breakthrough of the bioproducts occurs at the permeate outlet of the membrane module.

7. The method according to claim 1 further comprising purifying the bioproducts by passing an elution solution over the adsorbent particles disposed in the membrane module.

8. The method according to claim 1 further comprising passing an elution solution through the membrane and into contact with the adsorbent particles in order to purify the retained bioproducts.

9. The method according to claim 1 wherein the adsorbent particles are chromatographic matrix particles.

10. The method according to claim 1 wherein the adsorbent particles are adsorbent beads.

11. The method according to claim 1 wherein the adsorbent particles have an effective diameter of 5 micrometers or greater.

12. The method according to claim 1 wherein the adsorbent particles further comprise affinity ligands attached thereto.

13. The method according to claim 1 wherein the adsorbent particles reduce the differences in transmembrane pressure along the length of the feed solution flow path through the module.

14. The method according to claim 1 wherein the membrane is a microfiltration membrane.

15. The method according to claim 1 wherein the membrane is an ultrafiltration membrane.

* * * * *

UNITED STATES PATENT AND TRADEMARK OFFICE
CERTIFICATE OF CORRECTION

PATENT NO. : 6,022,477
DATED : February 8, 2000
INVENTOR(S) : Robert G. Juo, et. al.

It is certified that error appears in the above-identified patent and that said Letters Patent is hereby corrected as shown below:

Title page, item [54] and col. 1, change the title to read as follow:

--CHROMATOGRAPHIC METHOD FOR BIOMOLECULE PURIFICATION USING A HOLLOW-FIBER MEMBRANE MODULE--

Signed and Sealed this

Fourteenth Day of November, 2000

*Attest:*

*Attesting Officer*

Q. TODD DICKINSON
*Director of Patents and Trademarks*